(12) United States Patent
Reeve et al.

(10) Patent No.: US 7,768,647 B2
(45) Date of Patent: Aug. 3, 2010

(54) MULTI-COLOR CAVITY RINGDOWN BASED DETECTION METHOD AND APPARATUS

(75) Inventors: Scott Reeve, Jonesboro, AR (US); Susan Allen, Jonesboro, AR (US)

(73) Assignee: Arkansas State University - Jonesboro, State University, AK (US)

( * ) Notice: Subject to any disclaimer, the term of this patent is extended or adjusted under 35 U.S.C. 154(b) by 433 days.

(21) Appl. No.: 11/756,876

(22) Filed: Jun. 1, 2007

(65) Prior Publication Data

US 2009/0180119 A1 Jul. 16, 2009

Related U.S. Application Data

(60) Provisional application No. 60/803,757, filed on Jun. 2, 2006.

(51) Int. Cl.
*G01N 21/00* (2006.01)
(52) U.S. Cl. ...................... 356/437; 356/435
(58) Field of Classification Search ......... 356/432–440; 73/23.3, 23.2, 23.31; 250/227.18, 343, 559.4, 250/345, 339.12–339.13
See application file for complete search history.

(56) References Cited

U.S. PATENT DOCUMENTS

| | | | |
|---|---|---|---|
| 5,528,040 | A | 6/1996 | Lehmann |
| 6,075,252 | A | 6/2000 | Atkinson et al. |
| 6,975,190 | B2 | 12/2005 | Sato et al. |

| | | | | |
|---|---|---|---|---|
| 2003/0189711 | A1 | * | 10/2003 | Orr et al. .................. 356/484 |
| 2004/0065816 | A1 | | 4/2004 | Ye et al. |

OTHER PUBLICATIONS

Biennier, L., F. Salama, M. Gupta, and A. O'Keefe, Multiplex integrated cavity output spectroscopy of cold PAH cations, Chemical Physics Letters, 387, 287-294 (2004).
Clapper, M., J. Demirgian, and G. Robitaille, A Quantitative Method using FTIR to Detect Explosives and Selected Semivolatiles in Soil Samples, Spectroscopy, 10(7), 44-49 (1995).
Ding, Y., P. Macko, D. Romanini, V.I. Perevalov, S.A. Tashkun, J.L. Teffo, S.M. Hu, and A. Campargue, High Sensitiviy cw-Cavity Ringdown and Fourier Tranform Absorption Spectroscopies of 13CO2, Journal of Molecular Spectroscopy, 226, 146-160 (2004).
Esler, M.B., D.W.T. Griffith, S.R. Wilson, and L.P. Steele, Precision Trace Gas Analysis by FTIR Spectroscopy. I. Simultaneous Analysis of CO2, CH4, N2O andCO in air, Analytical Chemistry, 72(1), 206-215 (2000).
Fiedler, S.E., A. Hese, and A.A. Ruth, Incoherent broad-band cavity enhanced absorption spectroscopy, Chemical Physics Letters, 317, 284-294 (2003).

(Continued)

*Primary Examiner*—Gregory J Toatley, Jr.
*Assistant Examiner*—Tri T Ton
(74) *Attorney, Agent, or Firm*—Joe D. Calhoun; Rashauna A. Norment (57) ABSTRACT

A multi-color cavity ringdown based spectrometer is housed in a light tight enclosure to detect the presence of trace quantities of gas phase molecules emanating from explosives, drugs, or hazardous materials being transported through the enclosure or compounds contained in a patient's breath. A method is also disclosed for detecting gas phase molecules emanating from explosives, drugs, hazardous materials, or a patient's breath.

20 Claims, 8 Drawing Sheets

OTHER PUBLICATIONS

Ford, Alan R. and Scott W. Reeve, Sensing and Characterization of Explosive Vapors near 700 cm, SPIE Proceedings, Orlando 2007; Dept. of Chemistry and Physics AR State University, State University, AR USA 72467.

Gherman, T. and D. Romanini, Mode-locked cavity-enhanced absorption spectroscopy, 10(19), 1033-1041 (2002).

Gordon, S.M., J.P. Szidon, B.K. Kroloszynski, R.D. Gibbons, and H.J. O'Neill, Volatile Organic Compounds in Exhaled Air from Patients with Lung Cancer, Clin.Chem., 31(8), 1278-1282 (1985).

Haaland, D.M., R.G. Easterling, and D.A. Vopicka, Multivariate Least-Squares Methods Applied to the Quantitative Spectral Analysis of Multicomponent Samples, Applied Spectroscopy, 39(1), 73-84 (1985).

Janni, J., B.D. Gilbert, R.W. Field, J.I. Steinfeld, Infrared absorption of explosive molecule vapors, Spectrochimica Acta A, 53, 1375-1381 (1997).

O'Keefe, A. and D.A.G. Deacon, Cavity ringdown optical spectrometer for absorption measurements using pulsed laser sources, Review of Scientific Instruments, 59(12), 2544-2511 (1988).

O'Keefe, A., J.J. Scherer, and J.B. Paul, CW Intergrated Cavity Output Spectroscopy, Chemical Physics Letters, 307, 343-349 (1999).

O'Neill, H.J., S.M. Gordon, M.H. O'Neill, R.D. Gibbons, and J.P. Szidon, A Computerized Classification Technique for Screening for the Presence of Breath Biomarkers in Lung Cancer, Clin. Chem., 34(8), 1613-1618 (1988).

Reeve, S.W., and W.A. Weimer, Plasma Diagnostic of a direct-current arcjet diamond reactor. II. Optical emission spectroscopy, J.Vac. Sci. and Technol. A, 13(2) 359-367 (1995).

Reeve, S.W., W.A. Weimer, and D.S. Dandy, On the optimization of a dc arcjet diamond chemical vapor deposition reactor, J. Mater. Res., 11(3), 694-702 (1996).

Scherer, J.J., J.B. Paul, H. Jiao, and A. O'Keefe, Broadband ringdown spectral photography, Applied Optics 40(36), 6725-6732 (2001).

Singh, S. and M. Singh, Explosives detection systems for aviation security: A review, Signal Processing, 83, 31-55 (2003) and references therein.

Steinfeld, J.I., R.W. Field, M. Gardner, M. Canagaranta, S. Yang, A. Gonzalez-Casielles, S. Witonsky, P. Bhatia, B. Gibbs, B. Wilkie, S.L. Coy and A. Kachanov, New Spectroscopic Methods for Environmental Measurement and Monitoring, SPIE, 3853, 28-33 (1999).

Todd, M.W., R.A. Provencal, T.G. Owano, B.A. Paldus, A. Kachanov, K.L. Vodopyanov, M. Hunter, S.L. Coy, J.I. Steinfeld, and J.T. Arnold, Application of mid-infrared cavity-ringdown spectroscopy to trace explosives vapor detection using a broadly tunable (6-8 μm) optical paraureteric oscillator; Applied Physics B, 75, 367-376 (2002).

Totschnig, G., D.S. Baer, J. Wang, F. Winter, H. Hofbauer, and R.K. Hanson, Multiplexed continuous-wave diode laser cavity ringdown measurements of multiple species, Applied Optics, 39(12), 2009-2016 (2000).

Usachev, A.D., T.S. Miller, J.P. Singh, F.U. Yueh, P.R. Jang, and D.L. Monts, Optical Properties of Gaseous 2, 4, 6-Trinitrotoluene in the Ultraviolet Region, Applied Spectroscopy, 55(2), 125-129 (2001).

Wang, C., S.T. Scherrer, and D. Hossain, Measurements of Cavity Ringdown Spectroscopy of Acetone in the Ultraviolet and Near-Infrared Spectral Regions: Potential for Development of a Breath Analyzer, Applied Spectroscopy, 58(7), 784-791 (2004).

Wormhoudt, J., J.H. Shorter, J.B. McManus, P.L. Kebabian, M.S. Zahniser, W.M. Davis, E.R. Cespedes, and C.E. Kolb, Tunable infrared laser detection of pyrolysis products of explosives in soil, Applied Optics, 35(21), 3992-3997 (1996).

\* cited by examiner

MULTI-COLOR CAVITY RINGDOWN BASED DETECTION METHOD AND APPARATUS

RELATED APPLICATION

This application is a non-provisional of and claims priority under 35 U.S.C. §119(e) to provisional application 60/803,757 filed Jun. 2, 2006 entitled A Multi-Color Cavity Ringdown Based Detection Method and Apparatus.

FIELD OF THE INVENTION

The present invention relates to molecular absorption spectroscopy methods and apparatus, and in particular to those methods and apparatus which employ a multi-color optical cavity for increasing detection sensitivity, especially ones adapted for cavity ringdown spectroscopy. Additionally, this invention relates to an enclosure or portal apparatus employing a multi-color optical cavity for increasing detection sensitivity of gas phase molecules.

BACKGROUND OF THE INVENTION

The ideal optically based sensor combines a high selectivity towards the species of interest, a low Limit-of-Detection (LOD), and a real time sensing capability. High selectivity can often be obtained by utilizing a narrow-band (high resolution) light source or wavelength selection detection system. Spectroscopically speaking, an optical sensor can operate in either an absorption or emission mode. Certainly, emission based sensors can produce lower LOD in many cases. On the other hand, quantifying the spectral intensities from an emission based sensor to extract information regarding species concentrations is challenging due to inherent dynamical effects (quenching, predissociation, unknown quantum yields, etc.).

Direct absorption spectroscopy methods have many experimental advantages including selectivity and ease with which the absorbance measurements can be used to quantify species concentrations. While direct absorption measurements, at least the way in which the standard infrared absorption experiments are performed, do not possess the same level of detection sensitivity as fluorescence spectroscopic methods, there are specialized measures that can be incorporated into the experiment to overcome this limitation. For example, assuming Beer's Law can be applied to the absorption measurement and a previously optimized set of experimental conditions, it should be clear that improvements in the signal to noise ratio for the measurement can be realized by increasing the absorption path length. One strategy therefore, is to incorporate a multi-pass absorption sample cell into the experiment to effectively increase the path length through the sample. Indeed, by interfacing a 32 m White cell with a standard FTIR instrument, Robitaille and coworkers have demonstrated the ability to distinguish, identify and quantify 2,4-DNT, 2,6-DNT, and TNT vapor from heated soil samples with a ppm detection sensitivity. Clapper, M., J. Demirgian, and G. Robitaille, *A Quantitative Method using FTIR to Detect Explosives and Selected Semivolatiles in Soil Samples*, Spectroscopy, 10(7), 44-49 (1995).

Parenthetically, the problem of soil contamination at DOD and DOE facilities apparently represents a significant environmental problem. There are a number of federally funded studies focusing on the development of down-the-hole sensors for a variety of contaminants including explosives. As another example, spectroscopists from Aerodyne Research, utilizing a tunable Pb-salt diode laser coupled to an astigmatic Herriott cell reported both laboratory mechanistic as well as in situ field studies demonstrating a sensitive, specific, real time sensing capability for TNT in soils. Wormhoudt, J., J. H. Shorter, J. B. McManus, P. L. Kebabian, M. S. Zahniser, W. M. Davis, E. R. Cespedes, and C. E. Kolb, *Tunable infrared laser detection of pyrolysis products of explosives in soils*, Applied Optics, 35(21), 3992-3997 (1996). The TNT soil measurements reported in the literature utilized a thermal desorption system to entrain the soil contaminants into the gas phase.

Optical sensors designed to detect vapor emissions are not limited in scope or application to explosive or energetic materials. Many illicit drugs such as heroine or cocaine are often in chloride form. As a result, chlorine-containing compounds will often be detected in the vapor emissions from these compounds. Optically based vapor sensors also have potential applications as a medical diagnostic. There are over 300 volatile organic compounds (VOC's) in exhaled breath of humans. Gordon, S. M., J. P. Szidon, B. K. Krotoszynski, R. D. Gibbons, and H. J. O'Neill, *Volatile Organic Compounds in Exhaled Air from Patients with Lung Cancer*, Clin. Chem., 31(8), 1278-1282 (1985). The relative concentrations of VOC's have for centuries been used to assist in diagnosis. Patients suffering from diabetes tend to have elevated levels of ketones, principally acetone, in their breath for example, and hence often smell like rotten apples. More recently, patients suffering from breast cancer have been shown to have elevated levels of formaldehyde in their exhaled breath. O'Neill, H. J., S. M. Gordon, M. H. O'Neill, R. D. Gibbons, and J. P. Szidon, *A Computerized Classification Technique for Screening for the Presence of Breath Biomarkers in Lung Cancer*, Clin. Chem., 34(8), 1613-1618 (1988). The challenge for optical sensors in these cases is the ability to differentiate between normal and elevated levels of VOC's in a patient.

For many applications involving energetic materials, illicit substances, or medical diagnostics however, gaining an order of magnitude or two by increasing the absorption path length to 100 m or so may still not be sufficient. Consider that high quality military explosives need not be present in large quantities to cause significant damage particularly if combined with an incendiary compound. Persons with malicious intent can further exacerbate the vapor detection problem by encasing explosives in containers specifically designed to minimize vapor emissions. For medical diagnostic applications, the most useful sensor would be one capable of detecting elevated VOC levels at a pre-symptomatic, i.e., low concentration, stage.

In the late 1980's another direct absorption method was serendipitously discovered that allows absorption path lengths of 10 kilometers to be realized. O'Keefe, A. and D. A. G. Deacon, *Cavity ringdown optical spectrometer for absorption measurements using pulsed laser sources*, Review of Scientific Instruments, 59(12), 2544-2551 (1988). Called cavity ringdown laser absorption spectroscopy or "CRD", by its originators, it involves measuring changes in the characteristic ringdown time of a high Q optical cavity due to the presence of an absorbing sample. The ringdown cell is actually a type of lossmeter that was used initially to determine the reflectivity of high reflectance mirrors (R>99.9%). Over the past decade, cavity ringdown has been exploited by a number of research groups for a variety of applications. See for example, Busch, K. W. and M. A. Busch, Editors, *Cavity-Ringdown Spectroscopy: An ultratrace Absorption Measurement Technique*, ACS Symposium Series 720, American Chemical Society, Washington, D.C. 1999 and references therein. There have even been some preliminary studies to examine the potential of cavity ringdown for trace detection of explosive materials. Steinfeld, J. I., R. W. Field, M. Gardner, M. Canagaranta, S. Yang, A. Gonzalez-Casielles, S. Witonsky, P. Bhatia, B. Gibbs, B. Wilkie, S. L. Coy, and A. Kachanov, *New Spectroscopic Methods for Environmental Measurement and Monitoring*, SPIE, 3853, 28-33 (1999); Todd, M. W., R. A. Provencal, T. G. Owano, B. A. Paldus, A. Kachanov, K. L. Vodopyanov, M. Hunter, S. L. Coy, J. I. Steinfeld, and J. T. Arnold, *Application of mid-infrared cavity-ringdown spectroscopy to trace explosives vapor detection using a broadly tunable (6-8 □m) optical parameteric oscillator*, Applied Physics B, 75, 367-376 (2002); and Usachev, A. D., T. S. Miller, J. P. Singh, F.-U. Yueh, P.-R. Jang, and D. L. Monts, *Optical Properties of Gaseous 2,4,6-Trinitrotoluene in the Ultraviolet Region*, Applied Spectroscopy, 55(2), 125-129 (2001).

In the classic cavity ringdown experiment, a pulsed laser system serves as the radiation source. O'Keefe, A. and D. A. G. Deacon, *Cavity ringdown optical spectrometer for absorption measurements using pulsed laser sources*, Review of Scientific Instruments, 59(12), 2544-2551 (1988); and Busch, K. W. and M. A. Busch, Editors, *Cavity-Ringdown Spectroscopy: An ultratrace Absorption Measurement Technique*, ACS Symposium Series 720, American Chemical Society, Washington, D.C. 1999 and references therein. Output from this pulsed laser source is injected in a cavity consisting of two highly reflective mirrors (R>99.99%). Once injected into the cavity, the light pulse can traverse the cavity thousands of times, although a small portion of the intensity of the pulse leaks out of the cavity as each mirror is encountered. A detector is situated behind the mirror opposite the radiation input to monitor cavity output and/or decay of the laser pulse. For pulsed light sources, whose coherence length is short compared to the physical size of the cavity, the decay is typically exponential and possesses a decay or ringdown time characteristic for the cavity. In the presence of absorbing species, this characteristic ringdown time changes and hence absorption spectroscopy can by performed by measuring the difference in ringdown time as a function of molecular species concentration. For cavities with highly reflective mirrors, the absorption path length can approach 10 kilometers. The ultra-trace vapor detection potential of cavity ringdown is due then to this tremendous gain in path length compared with more traditional spectroscopic methods.

Prior CRD detection methods are deficient in that each of the methods take too much time to be useful in a real world environment. In the classic CRD laser experiment, an absorption spectrum, plotted as the intensity loss of the cavity versus wavelength, is actually composed of a great many individual cavity ringdown events. Collection of the absorption spectra or scan is initiated by first tuning the laser (or some other optical source) to a starting wavelength for the scan. A ringdown event is observed, averaged, and then modeled as an exponential decay in order to extract a characteristic ringdown time for the cavity at this starting wavelength and in the presence of an absorbing sample to be analyzed. Finally, this wavelength specific ringdown time, $\tau_{sample}(\lambda_{start})$, is compared with the ringdown time for an evacuated cavity, again at a specific wavelength, $\lambda_{start}$. This difference, $\beta = \tau_{empty}(\lambda_{start}) - \tau_{sample}(\lambda_{start})$, represents the first ordered pair in the absorption spectrum ($\beta_{start}, \lambda_{start}$). Of course an absorption spectrum includes a large number of such pairs. To continue collecting a spectrum, the laser must then be stepped or tuned to a new wavelength and the process repeated until an entire absorption spectrum has been obtained. Depending upon the size of the wavelength region to be scanned and/or the size of the individual steps for each retuning, such an experimental scheme can become quite time intensive (to the point of becoming time prohibitive for a real time sensor).

Driven by the molecular sensing potential of CRD methods, there have been a number of attempts to circumvent the time intensive nature involved with the collection of an absorption spectrum via the CRD method (which does not include the subsequent principal component analysis step required to quantify trace amounts of species in the gas sample). In some cases, a single averaged, wavelength specific, CRD event, chosen to coincide with the linecenter for a strong absorption peak in the spectrum, is used to perform the detection and quantification analysis. See for example, Wang, C., S. T. Scherrer, and D. Hossain, *Measurements of Cavity Ringdown Spectroscopy of Acetone in the Ultraviolet and Near-Infrared Spectral Regions: Potential for Development of a Breath Analyzer*, Applied Spectroscopy, 58(7), 784-791 (2004). Unfortunately, this strategy can severely limit the selectivity of the CRD method and, particularly for real world samples which can contain hundreds of compounds, effectively cripples the usefulness of the CRD approach. Other attempts to circumvent the time intensive collection challenge involve the use of a broadband laser or optical source. See for example, Scherer, J. J., J. B. Paul, H. Jiao, and A. O'Keefe, *Broadband ringdown spectral photography*, Applied Optics, 40(36), 6725-6732 (2001); and Biennier, L., F. Salama, M. Gupta, and A. O'Keefe, *Multiplex integrated cavity output spectroscopy of cold PAH cations*, Chemical Physics Letters, 387, 287-294 (2004). Indeed, O'Keefe and coworkers have demonstrated that such broadband light sources can in fact generate optical spectroscopic data for molecular species present only in trace amounts and in essentially real time. Scherer, J. J., J. B. Paul, H. Jiao, and A. O'Keefe, *Broadband ringdown spectral photography*, Applied Optics, 40(36), 6725-6732 (2001); and Biennier, L., F. Salama, M. Gupta, and A. O'Keefe, *Multiplex integrated cavity output spectroscopy of cold PAH cations*, Chemical Physics Letters, 387, 287-294 (2004). The trade off of course is that their broadband approach cannot achieve the same level of spectral resolution (and hence selectivity) as a narrow band laser source. In another incarnation of the broadband CRD concept, the output of a CRD cell was sent to a monochromator equipped with a diode-array or CCD detector. See Fiedler, S. E., A. Hese, and A. A. Ruth, *Incoherent broadband cavity enhanced absorption spectroscopy*, Chemical Physics Letters, 371, 284-294 (2003); and Gherman, T. and D. Romanini, *Mode-locked cavity-enhanced absorption spectroscopy*, Optics Express, 10(19), 1033-1041 (2002). Both groups have reported broadband CRD spectra with spectral resolution on the order of several tenths of a wavenumber resolution; certainly sufficient to rotationally resolve the molecules studied in these reports ($O_2$— Ruth and $C_2H_2$— Romanini). Unfortunately, this level of spectral resolution is insufficient to produce rotationally resolved spectra for larger molecules and, moreover, the experimental scheme described in these reports is not readily transferable to the fingerprint region of the infrared, primarily due to performance characteristics of monochromators, spectrographs, and linear array detectors.

The above discussed technical problems can be solved by the following apparatus. In essence a series of cw diode lasers, quantum cascade lasers, or other tunable laser sources, each tunable over a discrete, yet unique, fingerprint region of the infrared, will provide a capability to not only take advantage of the inherent sensitivity of the cavity ringdown method, but will also provide a high level of selectivity by allowing numerous fingerprint regions to be examined simultaneously. A PZT actuated mirror mount on each CRD cavity in the multicolor sample cell can facilitate use of these cw light sources. To ensure reliable and robust operation of the cavity ringdown instrument when interfaced with a scalable screening portal or other sampling device, hollow glass waveguides (HGW's) and/or infrared fiber optics can be utilized to interface each laser with the cavity ringdown detection cell. One of the limitations that has always been cited when comparing infrared or near infrared cavity ringdown methods with other infrared spectroscopic methods such as FTIR, is that while FTIR is orders of magnitude less sensitive, one can acquire a spectrum of the fingerprint region in less time. The invention disclosed herein effectively represents a solution to this limitation by allowing the measurement of multiple discrete fingerprint wavelengths simultaneously.

BRIEF DESCRIPTION OF THE DRAWINGS

These and other features, aspects and advantages of the present invention will become better understood with regard to the following description, appended claims and accompanying drawings, wherein:

SUMMARY OF THE INVENTION

A multi-color cavity ringdown based spectrometer is housed in a light tight enclosure to detect the presence of trace quantities of gas phase molecules emanating from compounds of interest entering the enclosure. In one embodiment of the invention, the compounds are explosives or drugs being transported through the enclosure. In another embodiment of the invention, the compounds are compounds contained in the exhaled breath of a person breathing into the enclosure. More specifically, the output from a laser source is coupled into a multicolor cavity ringdown sample cell by launching the radiation into a series of optical elements designed to match the optical mode characteristics of the CRD cavity, hereinafter, the telescope. Simultaneous ringdown measurements at multiple wavelengths are collected by utilizing a series of at least two cavity ringdown analysis systems, each having matched cavity ringdown cavities made of a pair of astigmatic highly reflective mirrors coated for a specific region of the infrared. The invention provides a broadband/multicolor capability through the use of several Pb-salt diode or quantum cascade ("QC") lasers, or other tunable lasers, each designed to lase in a different spectral region. Each individual laser is coupled with a different set of CRD mirrors, optimized with a reflectivity bandwidth for that particular laser all mounted on a single gas sample cell. A telescope is included to mode match the radiation with the individual cavity ringdown cavities.

To circumvent the time intensive protocol associated with generating a CRD absorption spectrum for the gas sample, i.e., observation of a wavelength dependent ringdown event, average, analyze, retune/step laser to next wavelength, observe wavelength dependent ringdown event, etc., we combine a multicolor laser approach with the ICOS method of O'Keefe et. al. O'Keefe, Scherer, and Paul, U.S. Pat. No. 6,975,190 B1, 2004; and O'Keefe, A., J. J. Scherer, and J. B. Paul, *CW Integrated Cavity Output Spectroscopy*, Chemical Physics Letters, 307, 343-349 (1999). The ICOS variation of cavity ringdown involves mounting one of the cavity mirrors on a piezoelectric transducer ("PZT") actuated mirror mount. Here the transmission fringe problem can be eliminated through the clever application of an amplitude modulation voltage to the PZT. Thus, linear cavity ringdown absorption spectra can be obtained with cw laser sources using the ICOS method without the need for expensive acousto-optic modulators or other optical isolating devices. By rapidly scanning each individual laser over a single longitudinal mode an absorption spectrum for all regions of spectroscopic interest with detection sensitivities similar to those afforded by the more traditional CRD methods is obtained.

This approach is different from the other previously disclosed multicolor and/or multiplexed diode laser instruments. See for example, Totschnig, G., D. S. Baer, J. Wang, F. Winter, H. Hofbauer, and R. K. Hanson, *Multiplexed continuous-wave diode laser cavity ringdown measurements of multiple species*, Applied Optics, 39(12), 2009-2016 (2000). In the case of Hanson and coworkers, they describe a system consisting of two near infrared diode lasers of nearly identical wavelength output and perform their experiment by sequentially sending radiation from first one laser and then the other through a single set of CRD mirrors. Both Hanson et. al. and Lukow describe a experimental protocol incorporating the observe, average, analyze, and retune approach to performing the CRD measurements. Totschnig, G., D. S. Baer, J. Wang, F. Winter, H. Hofbauer, and R. K. Hanson, *Multiplexed continuous-wave diode laser cavity ringdown measurements of multiple species*, Applied Optics, 39(12), 2009-2016 (2000); and Lukow, http://chem.tufts.edu/PropDataBase/Stefan Prop.pdf, 2002. Neither of these approaches appears to have a real time capability, effectively limiting their potential as a molecular sensor.

Another distinguishing aspect of this approach is the molecular species used in the sensing process. In the case of explosive and/or energetic compounds, most approaches tend to focus on the spectral signature for the pure energetic material. Many of these explosive compounds have extremely low vapor pressures making the challenge of detecting the pure material quite significant. Moreover, explosive devices are often enclosed in hermetic containers and/or hidden effectively lowering the material's vapor pressure by several orders of magnitude making detection of even an explosive such as TNT (trinitrotoluene), which possesses a relatively high vapor pressure at room temperature (10 parts per billion by volume), well beyond the limits of current technology. To circumvent this seemingly insurmountable challenge, the approach described here can utilize a series of characteristic signatures for explosive detection in addition to or instead of utilizing the signature of the substance itself. These characteristic signatures are due to naturally occurring impurities in energetic compounds and are believed to constitute the bouquet of odors trained canines use for locating, identifying, and detecting explosives. In the case of TNT based explosives, this bouquet is composed of spectral signatures from toluene, nitrobenzenes (principally the mono- and di-variations), and nitrotoluenes (there are several mono- and di-structural isomers). For RDX based explosives (including C4), cyclohexanone appears to be the primary constituent of the bouquet. Acetone is the species to be sensed for TATP (triacetone triperoxide) based explosives.

The rotationally resolved spectral signatures for many of these explosive bouquet compounds are not currently available in the literature. As part of this approach a spectroscopic library containing the required spectral information is currently being developed for sensing applications. Most of these bouquet molecules are not only classified as asymmetric tops, they are fairly large molecules from a high resolution spectroscopy perspective. Obtaining rotationally resolved spectra for such molecules is often impossible without utilizing molecular beam and/or supersonic jet cooling techniques. However we were able to obtain rotationally resolved infrared spectra for a number of these explosive bouquet molecules as well as identify a number of wavelength regions suitable for sensing applications without jet cooling methods by spectroscopically measuring these bouquet compounds at trace concentration levels with a long pathlength absorption cell. Under these conditions, only the most intense spectral features can be observed. The individual spectra shown in FIGS. 5-8 represent the first reported rotationally resolved infrared measurements for toluene, nitrobenzene, and o-mononitrotoluene in the 650-750 $cm^{-1}$ region (Ford and Reeve, in press).

Medical diagnostic applications represent a different sort of challenge from those described above for explosive detection. For biomedical sensing, the instrument must not only be capable of detecting trace amounts of biomarkers the complicated matrix of exhaled breath, but must also possess the sensitivity to distinguish between normal levels and elevated levels of a particular biomarker. Although in some cases, the biomarkers for medical diagnostic applications are similar to those in explosive detection. For example, acetone is both a target for TATP detection and sensing as well as being a biomarker for diabetes in humans.

DETAILED DISCLOSURE OF THE INVENTION

Figure 1:
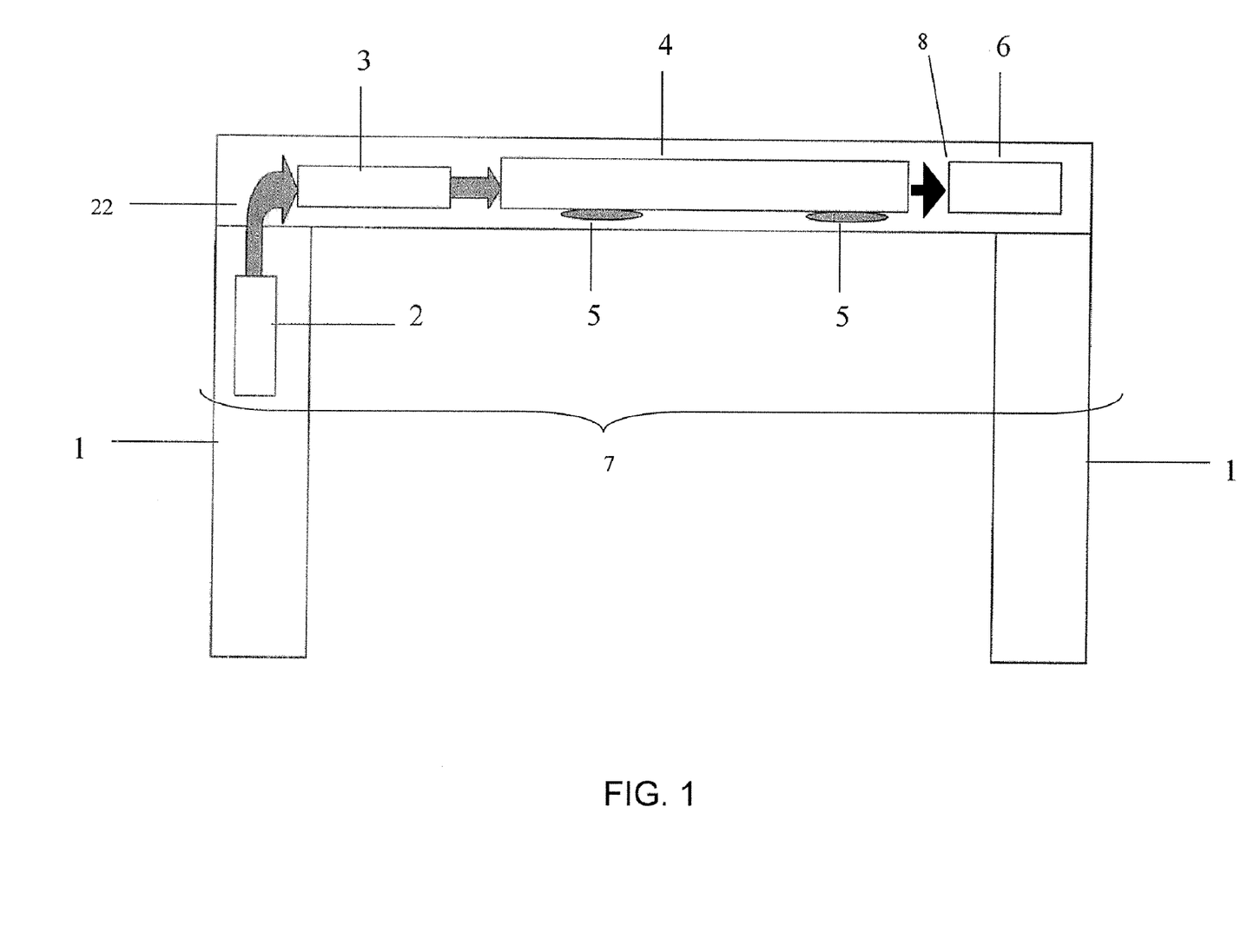
FIG. 1 is an overall schematic of the invention depicting a detection enclosure of unspecified dimensions.
Figure 2:
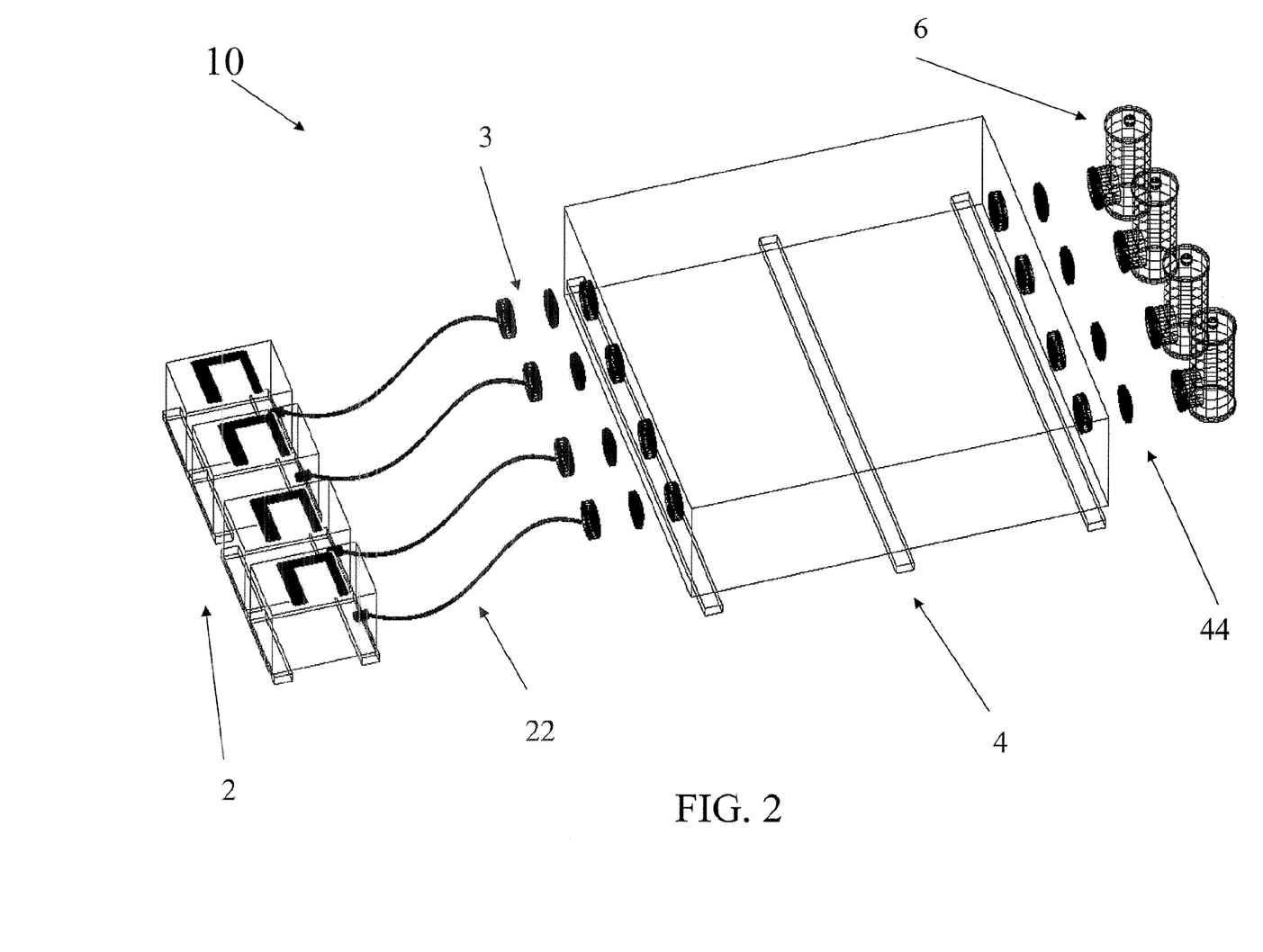
FIG. 2 is a schematic of an expanded view of the cavity ringdown detection spectrometer inside the enclosure not shown, depicting one embodiment comprising 4 lasers, each providing radiation to a separate respective pair of opposing mirrors establishing a respective optical cavity, each respective optical cavity providing radiation to a separate photometric detector, all four optical cavities housed within a single gas sample cell.

In FIGS. 1 and 2 there is illustrated a multi-color absorption spectroscopy apparatus 10 for detecting certain molecules in the gas phase, made of a set of at least two cavity ringdown analysis systems 7, a photometric detector 6 to receive and analyze radiation emitted from each of the cavity ringdown cells 4 in the cavity ringdown analysis systems 7, and means 5 for receiving a gas into cavity ringdown laser-based detection cells, hereinafter "cavity ringdown cells" 4 in the cavity ringdown analysis systems 7 for analysis. FIG. 2 shows four cavity ringdown analysis systems 7 with photometric detectors 6. A cavity ringdown analysis system 7 made of a laser 2 emitting radiation at a wavelength, means 22 for transporting the radiation from the laser; a telescope 3, receiving the radiation from the means 22 for transporting and emitting the radiation, and a cavity ringdown cell 4, receiving the radiation from the telescope 3 and emitting the radiation to go to the photometric detectors 6. The wavelengths of the radiation emitted from each of the lasers 2 are different.

In the preferred embodiment of the invention, the apparatus 10 described above is either contained in a light tight enclosure 1 as displayed in FIG. 1 wherein the light tight enclosure 1 has means to receive gas phase emissions or contained in a light tight enclosure 1 attached to a tube, not shown, into which a user could breathe to introduce breath to be analyzed into the apparatus. Below, the device and how it works are described in more detail.

Now referring to FIG. 1, a light tight enclosure 1 is shown. In one embodiment, the light tight enclosure 1 is of sufficient size to receive an object (not shown) to be analyzed for at least one gas phase molecule. Dimensions can be scaled to allow the light tight enclosure 1 to scan cargo/vehicles as well as individuals. The object to be analyzed can be a vehicle, such as a truck, a container, such as a shipping container, or individuals. In another embodiment, the enclosure 1 can be connected to a tube (not shown) to receive the exhaled breath of a user (not shown) to be analyzed for at least one gas phase molecule. The term at least one gas phase molecule means that at least one specific type of molecule can be detected. Housed within the light tight enclosure 1 is a set of at least two cavity ringdown analysis systems 7, each made of a cavity ringdown cell 4 and telescope 3, a laser 2 emitting radiation at a wavelength, sample collection and preparation apparatus 5, light detectors 8 and associated photometric detectors 6. The light tight enclosure 1 includes a set of at least two different color lasers 2. In the preferred embodiment, the different color lasers are Pb-salt diode lasers or quantum cascade lasers. The set of at least two different color lasers 2 is operationally connected to a set of telescopes 3. There is one telescope 3 connected to each laser 2. The function of each telescope 3 is to couple the radiation into the cavity ringdown cell 4. The radiation can enter the telescope 3 by a means 22 for transporting the radiation from the laser 2; for example a hollow glass waveguide or appropriate fiber optic cable. While conventional optics could be also be used to transport the radiation, in the preferred embodiment, fiber optics (or a set of HGWs) give the device added robustness. The cavity ringdown cell 4 including a means 5 to receive a gas phase sample. While a chromatography and/or separation method for removing water and other interfering materials from species of interest could, in principle, be used for this purpose, in the preferred embodiment the means 5 to receive a sample includes at least one molecular sieve and a pre-concentrator bar, as described below, to direct selected materials into the cavity ringdown 4. Additionally, this apparatus 10 includes a set of at least two photometric detectors 6 for photometric detection of at least one chemical molecule. There is one detector 6 for each laser 2.

FIG. 2 is a schematic in an expanded view of the apparatus 10 from the set of at least two different color lasers 2 to the cavity ringdown cell 4 inside the light tight enclosure 1 showing the set of at least two different color lasers 2, the means 22 for transporting the radiation from the laser, which could be, for example, hollow glass waveguides and/or fiber optics to guide the laser radiation to the telescope 3, and the cavity ringdown cell. All of the lasers 2 will have output in the mid-infrared region of the electromagnetic spectrum, also known as the fingerprint region.

Figure 3:
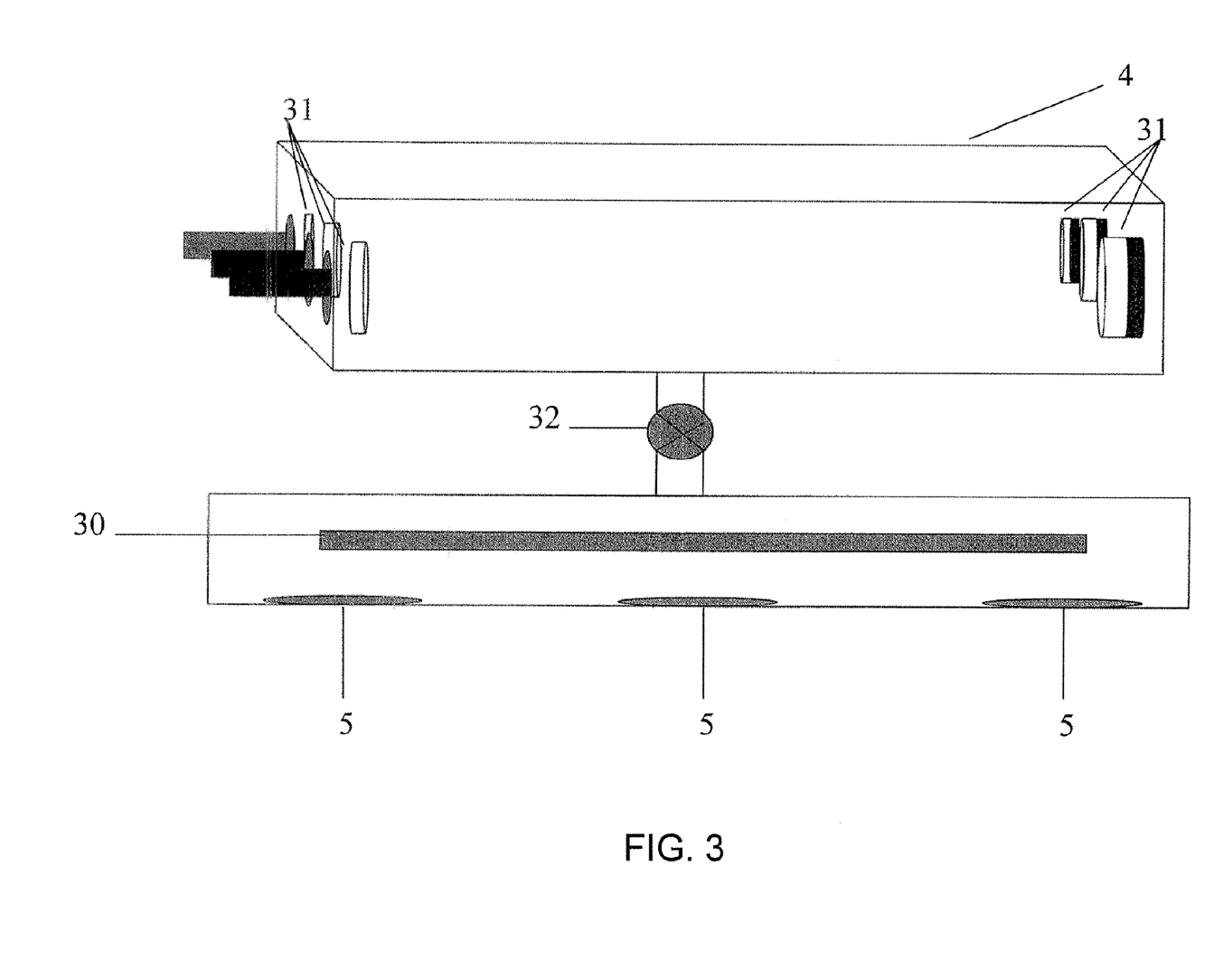
FIG. 3 is a schematic drawing of the cavity ringdown detection cell.

FIG. 3 shows the cavity ringdown detection cell 4 containing a number of sets of astigmatic mirrors 31 each optimized for a different region in the infrared. There will be one set of mirrors 31 (representing an individual cavity ringdown cavity) for each laser 2. In the preferred embodiment, the means 5 to receive a gas phase sample will be effectuated as follows: air samples to be analyzed will first be passed through a set of molecular sieves 5 and will then interact with a sample preparation apparatus 30, i.e. a pre-concentrator bar. This sample preparation apparatus 30 will have the capability to be sequentially cooled to trap materials to be detected and then flash heated to inject these materials into the cavity ringdown cell 4 through valve 32 for identification and quantification of molecular species present.

Figure 4:
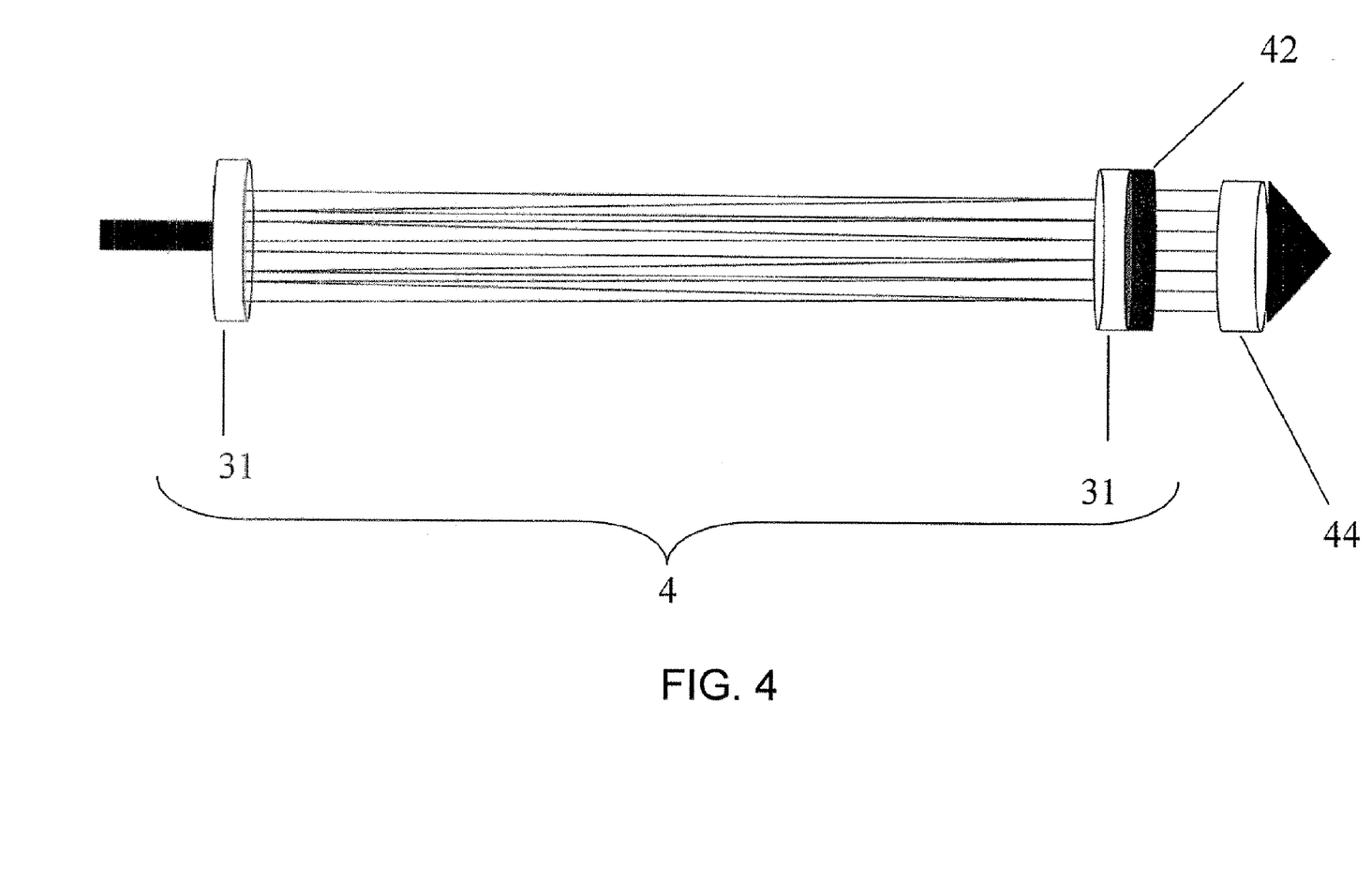
FIG. 4 is a schematic drawing of one pair of opposing mirrors, with optical input and output, establishing an individual optical cavity within a single gas sample cell (not shown).

FIG. 4 shows one of the individual sets of astigmatic mirrors 31 mounted within the cavity ringdown cell 4. Note the PZT actuate mirror mount 42 on one of the mirrors. Following the cw ICOS approach to cavity ringdown introduced by Paul, Scherer, and O'Keefe, U.S. Pat. No. 6,795,190 column 4 line 65 through column 9 line 22 (hereby specifically incorporated by reference in its entirety) the effective cavity length of each individual cavity ringdown cavity is modulated over a number of cavity modes while rapidly scanning each diode laser through a single longitudinal mode. Upon exiting the cavity cell 4, the radiation is focused through a lens 44 onto a standard photometric detector 6. In the preferred embodiment, the detector is a Mercury Cadmium Telluride ("MCT") detector. Detector signals are sent to a computer for further analysis.

The spectral analysis issue warrants some additional explanation. In the classic cavity ringdown experiment, a series of ringdown events, obtained over a sequential set of wavelengths, constitutes an absorption spectrum. Actually it is the change in the characteristic ringdown time for a cavity containing an absorbing species (compared to that of an empty cavity) that is the quantity of interest from a spectroscopic perspective. Thus, the absorption spectrum can be defined as a plot change in ringdown time for the cavity versus wavelength. With an absorption spectrum in hand, standard methods for extracting concentrations are readily available. See for example, Bernath, P. F., Spectra of Atoms and Molecules, Oxford University Press, New York, N.Y. 1995. Of course, generating an absorption spectrum in the classic cavity ringdown manner can be a time consuming undertaking to the point of being time prohibitive for the applications described in this disclosure. For many ultra-trace detection applications, many published reports describe using a ringdown event at a single wavelength (albeit one corresponding to an absorption maximum for the species of interest) to circumvent the time prohibitive limitation. Unfortunately, this strategy may not be effective for a real world sample containing potentially interfering (but yet innocuous) compounds.

The invention addresses this potentially challenging limitation in two fundamental ways. First, using the modified cavity ringdown method of O'Keefe et. al. O'Keefe, Scherer, and Paul, U.S. Pat. No. 6,975,190 B1, 2004; and O'Keefe, A., J. J. Scherer, and J. B. Paul, *CW Integrated Cavity Output Spectroscopy*, Chemical Physics Letters, 307, 343-349 (1999), known as ICOS, absorption spectra are collected by modulating both the cavity ringdown cell mirror and the diode laser albeit with detection sensitivity inherent with the cavity ringdown absorption technique. Second, the invention can collect ICOS absorption spectra for several different fingerprint regions of the infrared simultaneously by simultaneously modulating or scanning several different lasers. In other words, this invention does not suffer from the potential time prohibitive limitation of other previously published cavity ringdown embodiments, while at the same time it retains the high degree of selectivity inherent in Pb-salt diode and/or quantum cascade laser systems. Finally, the invention can utilize a unique approach for the sensing of explosive compounds by focusing on vapor signatures from a series of naturally occurring impurities in the explosives in addition to or instead of the pure explosive material itself. In essence, the invention is designed to mimic the trained canine nose in terms of molecular species used to produce an alert or positive response and represents a fundamental shift in optically based explosive sensing design and development.

Figure 5:
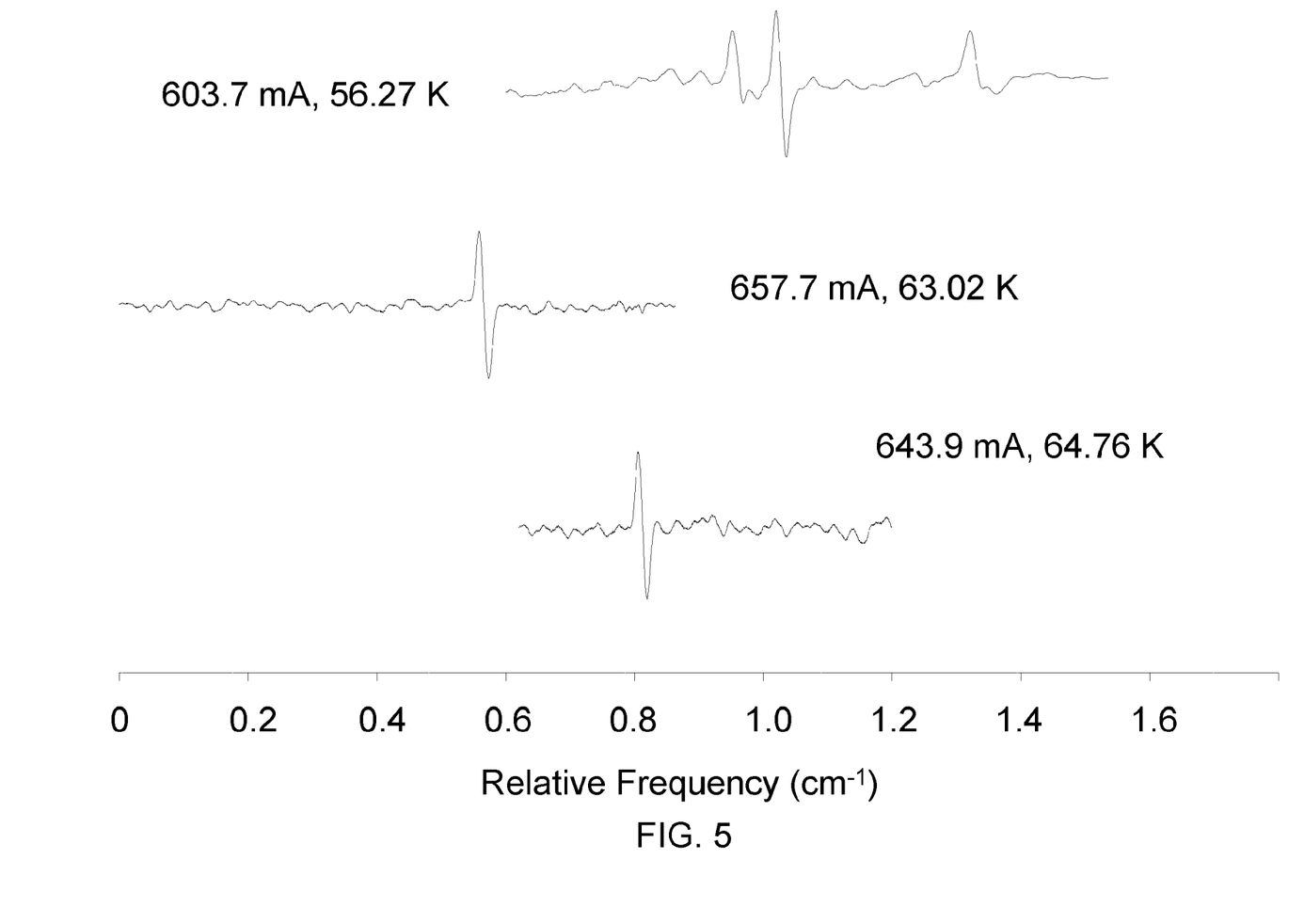
FIG. 5 shows several discrete portions of the rotationally resolved vibrational spectrum of toluene in the 13-15 micron range. Each trace represents a first derivative single scan (no signal averaging) over a distinct longitudinal mode of a Pb-salt laser. The traces are plotted in terms of relative frequency for convenience. The starting point for each scan appears offset due to the differences in longitudinal lasing mode characteristics and the manner in which an automated LabVIEW calibration routine operates. Pb-salt diode laser current and temperature settings are also listed for each scan.
Figure 6:
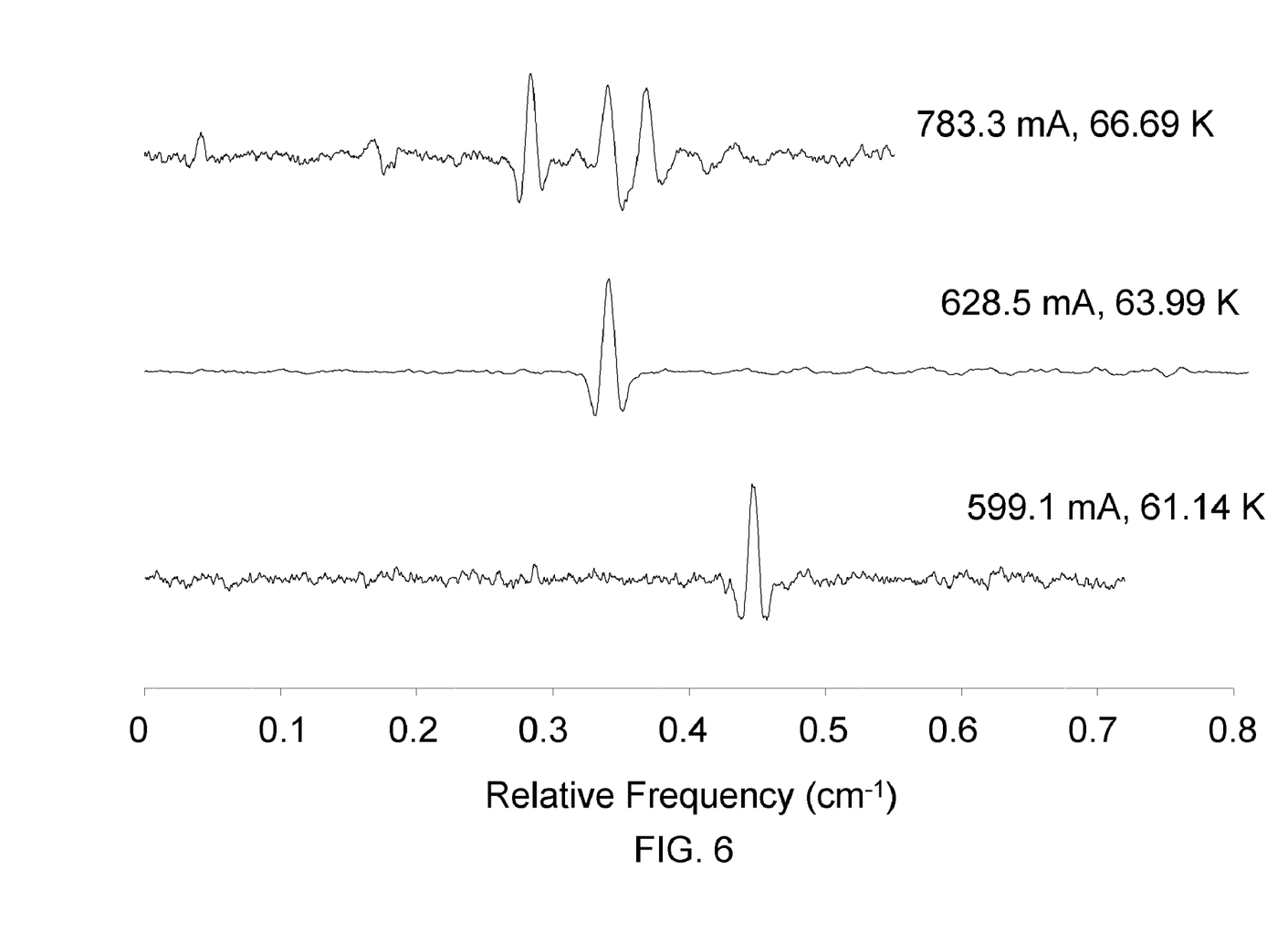
FIG. 6 shows several discrete portions of the rotationally resolved ring bending mode for nitrobenzene in the 13-15 micron region.
Figure 7:
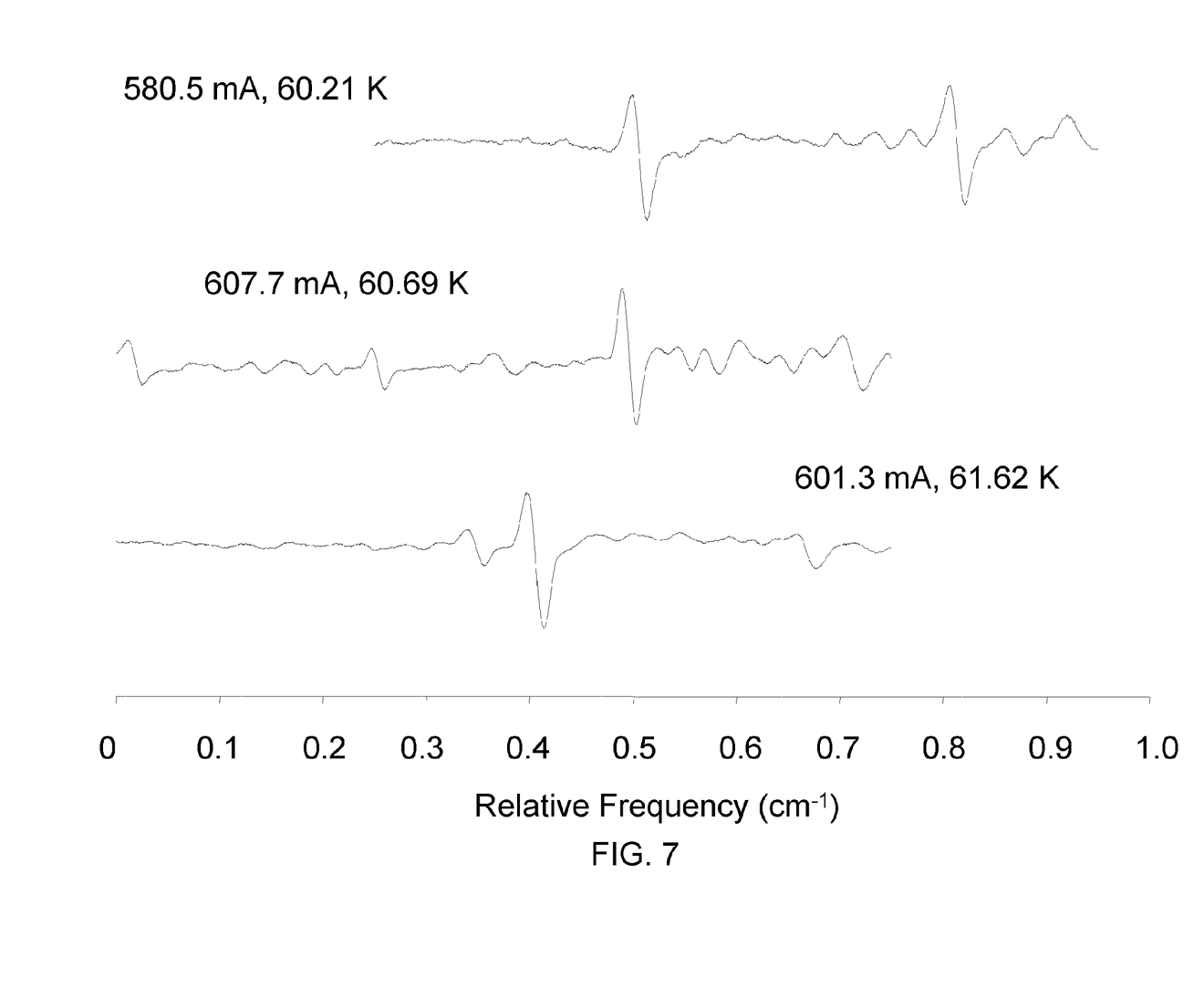
FIG. 7 shows several discrete portions of the rotationally resolved ring bending mode for o-mononitrotoluene in the 13-15 micron region.
Figure 8:
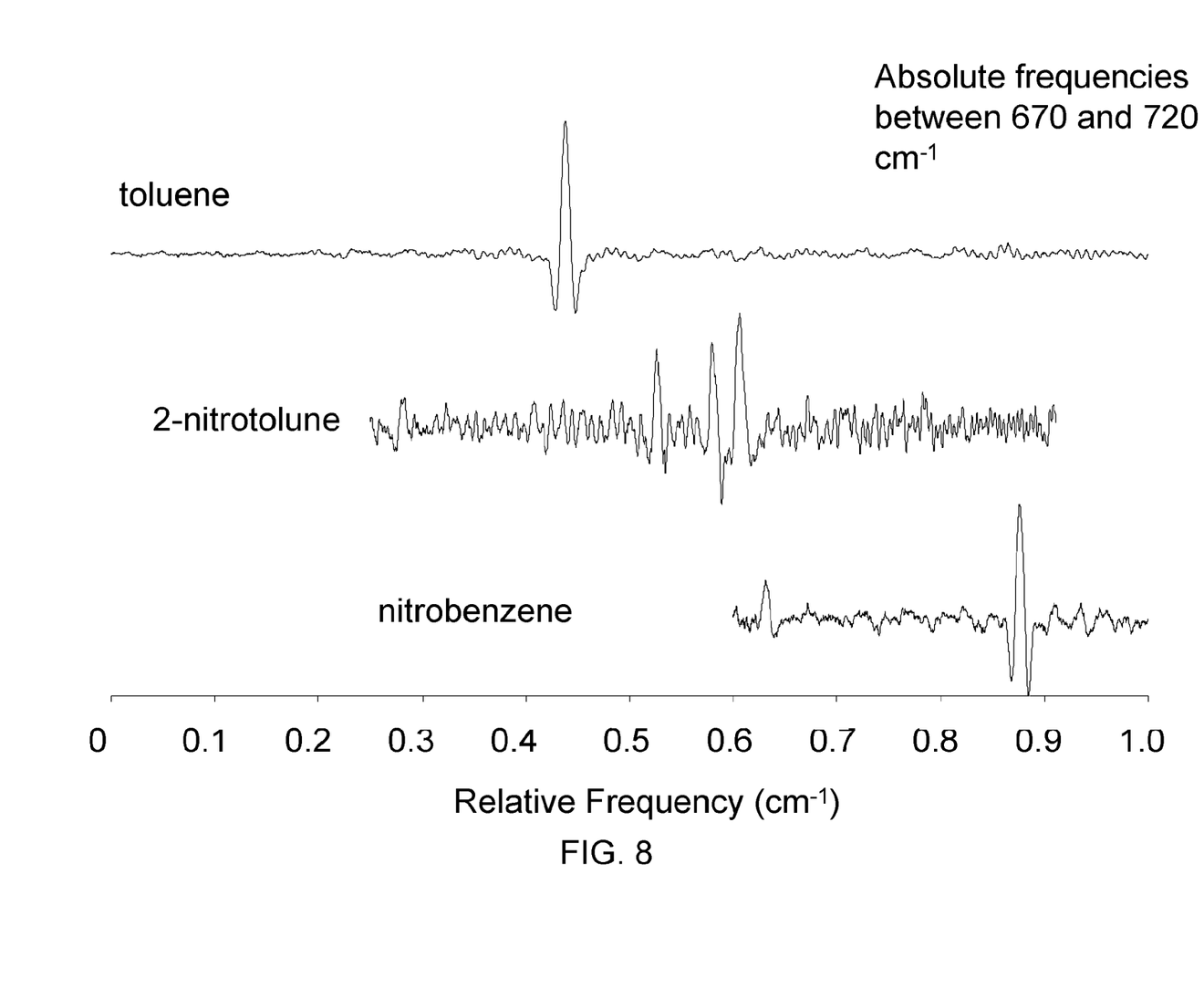
FIG. 8 shows a series of second derivative rotationally resolved absorption measurements obtained with a simulated explosive bouquet sample in the 13-15 micron range. The top trace is due to toluene in the sample, the middle trace nitrobenzene, and the bottom trace is an o-mononitrotoluene signature. The data was collected by sequentially tuning a single Pb-salt diode laser appropriate wavelength regions for each species in the bouquet.

In FIGS. 5, 6, and 7, portions of the spectroscopic database for toluene, nitrobenzene, and o-mononitrotoluene, collected with a single Pb-salt diode laser system, are shown. Each of these traces depicts spectral regions that could potentially be utilized for sensing applications. To date, dozens of spectral transitions have been measured, catalogued and recorded for toluene, nitrobenzene, o-mononitrotoluene, and m-nitrotoluene. Ford, A. R. and S. W. Reeve, *Sensing and Characterization of Explosive Vapors near 700 $cm^{-1}$*, SPIE Proceedings, 6540, in press. To demonstrate the utility of this approach, FIG. 8 shows a series of traces obtained by sequentially tuning a single Pb-salt diode laser to sensing regions for toluene, nitrobenzene, and o-nitrotoluene. The measurements in FIG. 8 were performed on a simulated explosive bouquet created by bubbling a 1000 ppm toluene in argon gas sample though a solution containing equal parts of nitrobenzene and o-nitrotoluene. Total pressure in the sample cell during spectra collection was 1-5 torr. All of the data included here were collected in the 660-720 $cm^{-1}$ frequency range. The highly reflective mirrors required to perform cavity ringdown measurements are not, at present, commercially available for this spectral region and thus a more conventional long path absorption cell was incorporated into the system to make these proof-of-concept measurements.

For real world analysis problems, it is necessary to be able to extract concentrations for species of interest (illicit substances and/or medically important diagnostics) from absorption spectra. While there are a number of standard algorithms in the literature for performing such a principal component analysis. See for example, Esler, M. B., D. W. T. Griffith, S. R. Wilson, and L. P. Steele, *Precision Trace Gas Analysis by FTIR Spectroscopy. 1. Simultaneous Analysis of $CO_2$, $CH_4$, $N_2O$, and CO in air*, Analytical Chemistry, 72(1), 206-215 (2000); and Haaland, D. M., R. G. Easterling, and D. A. Vopicka, *Quantitative Spectral Analysis of Multicomponent Samples*, Applied Spectroscopy, 39(1), 73-84 (1985), the current embodiment uses an algorithm originally designed to extract gas phase concentrations from convoluted mass spectral data. Reeve, S. W., W. A. Weimer, and D. S. Dandy, *On the optimization of a dc arcjet diamond chemical vapor deposition reactor*, J. Mater. Res., 11(3), 694-702 (1996). The mass spectral algorithm was built around a fitting function of the form $$S_i = \sum_i F_i C_i \quad (1)$$

where $S_i$ is the signal strength at a particular mass to charge ratio, $F_i$ the fractional contribution of species i to the signal strength and $C_i$ the concentration of species i. For the mass spectral data problem, the $F_i$ component represents essentially the observed cracking pattern for the species under consideration. In the current embodiment, the fitting function is modified as follows $$S_\lambda = \sum_i F_{\lambda i} C_i + bg_\lambda. \quad (2)$$

The fractional contribution at each wavelength, $F_{\lambda,i}$, is no longer simply the experimentally observed cracking pattern, but is now a product of the line absorption spectrum for a particular species i, calculated using the known molecular constants from the literature for that species, and a lineshape function. Reeve, S. W., and W. A. Weimer, *Plasma Diagnostics of a direct-current arcjet diamond reactor. II. Optical emission spectroscopy*, J. Vac. Sci. and Technol. A, 13(2), 359-367 (1995). The $bg_\lambda$ term in the expression above represents the background component in the observed signal. In order to extract the concentration of species contributing to the observed signal, a simulated spectrum is generated via equation (2) using some initial set of concentrations and then is compared with an absorbed spectrum obtained by the multicolor ICOS device. In real time, the simulated spectrum is forced to reproduce the observed spectrum by making a series of iterative changes to the species concentration. In this manner, the species concentration information is extracted from the observed data.

Although the present invention has been described and illustrated with respect to preferred embodiments and a preferred user thereof, it is not to be so limited since modifications and changes can be made therein which are within the full scope of the invention.

The invention claimed is:

1. A multi-color absorption spectroscopy apparatus for detecting certain molecules in the gas phase, comprising:
    a set of at least two cavity ringdown analysis systems, each comprising:
        a laser emitting radiation at a wavelength;
        means for transporting said radiation from said laser;
        a mode matching telescope, receiving said radiation from said means for transporting and emitting said radiation; and
        a cavity ringdown cell having at least a pair of opposing mirrors optimized for the bandwidth of maximum reflectivity corresponding to the tuning range of the respective radiation, receiving said radiation from said telescope and emitting said radiation, said cavity ringdown cell having a cavity into which it can receive a gas for analysis;
    wherein said wavelengths of said radiation emitted from said lasers are each different by at least five percent (5%) of the center of the optimized wavelength range;
    a photometric detector to receive and analyze said radiation emitted from each of said cavity ringdown cells in each of said cavity ringdown analysis systems; and
    means for receiving a gas into said cavity ringdown cells in said cavity ringdown analysis systems for analysis.

2. A multi-color absorption spectroscopy apparatus described in claim 1, further comprising a light tight enclosure sized to accommodate an object to be scanned for the absorption of at least one gas phase molecule, wherein said enclosure includes means to receive said gas phase absorption and said enclosure includes the multi-color absorption spectroscopy apparatus of claim 1.

3. The multi-color absorption spectroscopy apparatus of claim 1 further comprising a tube for receiving the breath to be analyzed from a user.

4. A multi-color absorption spectroscopy apparatus for detecting certain molecules in the gas phase sample, comprising:
    (a) a plurality of lasers, each emitting radiation at a wavelength different from the other laser(s) and each optically coupled to;
    (b) a respective pair of opposing mirrors comprising a cavity ringdown optical cavity, all of said optical cavities housed within the same gas sample cell, each of said optical cavities outputting the respective radiation to;
    (c) a respective photometric detector for analysis simultaneously with analysis of other respective radiation by another respective photometric detector; and
    (d) a light tight enclosure enclosing at least said photometric detectors and cell housing said optical cavities, said enclosure comprising a gas receiving means for receiving a sample of gas for the analyses.

5. A method of detecting the presence of at least one gas phase molecule comprising:
    (a) providing the light tight enclosure of the apparatus of claim 4 and actuating a plurality of lasers of said apparatus;
    (b) transporting a source of gas phase molecules near the gas receiving means of said enclosure to provide a gaseous sample for simultaneous analyses; and
    (c) detecting the presence of at least one gas phase molecule.

6. A method, described in claim 5, of detecting the presence of at least one low vapor pressure hazardous material, said simultaneous analyses detecting a complex of gas phase impurity and decomposition molecules characteristic of that particular hazardous material.

7. A method, described in claim 5, of detecting a complex of gas phase molecules in the breath of a user, said gas receiving means comprising a breath exhalation capture chamber, said source of gas phase molecules is a human exhaling into said breath exhalation chamber, and said simultaneous analyses detecting the complex of gas phase molecules.

8. A method, described in claim 5, of detecting the presence of at least one low vapor pressure hazardous material, drug or explosive material in a shipping container, the transporting of the source of gas phase molecules comprising conveyance of the shipping container near the gas receiving means to provide a gaseous sample for simultaneous analyses detecting a complex of gas phase impurity and decomposition molecules characteristic of that particular hazardous material, drug or explosive.

9. A method, described in claim 5, of detecting, in the breath of a user, the absence of at least one gas phase molecule, said gas receiving means comprising a breath exhalation capture chamber, and said source of gas phase molecules is a human exhaling into said breath exhalation chamber, said simultaneous analyses detecting the absence of at least one gas phase molecule.

10. A method, described in claim 5, of detecting, in the breath of a user, the presence of at least one gas phase molecule, said gas receiving means comprising a breath exhalation capture chamber, and said source of gas phase molecules is a human exhaling into said breath exhalation chamber.

11. A multi-color absorption spectroscopy apparatus of claim 4, the reflectivity of each respective mirror being optimized for the bandwidth of maximum reflectivity corresponding to the tuning range of the respective radiation.

12. A multi-color absorption spectroscopy apparatus of claim 11, the difference between said optimization for one optical cavity and for another optical cavity being greater than about five percent (5%) of the center of the optimized wavelength range.

13. A multi-color absorption spectroscopy apparatus of claim 4, further comprising a piezoelectric transducer actuated mirror mount for one of said optical cavity mirrors.

14. A multi-color absorption spectroscopy apparatus of claim 11, further comprising transport means for transporting said radiation from said laser and said housing, selected from the group consisting of hollow glass waveguides, fiber optic cabling, mirrors, lenses and telescopes, and combinations thereof.

15. A multi-color absorption spectroscopy apparatus of claim 14, said transport means comprising a mode matching telescope between a respective laser and a respective optical cavity.

16. A multi-color absorption spectroscopy apparatus of claim 4, said lasers are selected from the group consisting of Pb-salt diode lasers, quantum cascade lasers and other tunable lasers, and combinations thereof capable of continuous wave or non-continuous wave emissions.

17. A multi-color absorption spectroscopy apparatus of claim 4, said gas receiving means of said enclosure selected from the group consisting of an exhalation capture chamber, molecular sieve and a pre-concentrator bar, and combinations thereof.

18. A multi-color absorption spectroscopy apparatus of claim 4, all of said lasers emitting radiation in the mid-infrared region of the electromagnetic spectrum.

19. A multi-color absorption spectroscopy apparatus of claim 4, further comprising a computer with analytical programming for comparing the cavity ringdown absorption profile of the sample against a library of cavity ringdown absorption spectrum profiles of target substances.

20. A multi-color absorption spectroscopy apparatus of claim 4, said spectral signature generation or detection occurring in less than 5 seconds.

* * * * *